United States Patent [19]

Morrison et al.

[11] 4,211,487

[45] Jul. 8, 1980

[54] METHOD AND APPARATUS FOR DETERMINING AEROSOL SIZE DISTRIBUTIONS

[75] Inventors: Clyde A. Morrison, Wheaton; Nick Karayianis; Donald E. Wortman, both of Rockville, all of Md.

[73] Assignee: The United States of America as represented by the Secretary of the Army, Washington, D.C.

[21] Appl. No.: 4,979

[22] Filed: Jan. 22, 1979

[51] Int. Cl.$^2$ .............................................. G01N 15/02

[52] U.S. Cl. ...................................... 356/336; 250/574

[58] Field of Search ................. 356/336, 318; 250/574

[56] References Cited

FOREIGN PATENT DOCUMENTS 1179385 6/1961 Fed. Rep. of Germany ........... 356/336

*Primary Examiner*—John K. Corbin
*Assistant Examiner*—Bruce Y. Arnold
*Attorney, Agent, or Firm*—Nathan Edelberg; Robert P. Gibson; Saul Elbaum

[57] ABSTRACT

A method and apparatus for determining aerosol size distributions, in which the droplets of an aerosol region are placed in an amplitude modulated electric field, which produces resonant elongation and contraction of particularly sized droplets, in the form of mechanical oscillations, depending on the modulating frequency of the modulated electric field. A light beam is directed against the oscillating droplets and scattered thereby, with the intensity of the scattered light beam varying as a result of the changing reflection surfaces presented by the oscillating droplets. Differently sized drops are sequentially resonantly oscillated by selectively varying the modulation frequency of the electric field, with the varying intensity of the oscillating droplets at each modulation frequency yielding the size distribution of a given aerosol.

4 Claims, 3 Drawing Figures

METHOD AND APPARATUS FOR DETERMINING AEROSOL SIZE DISTRIBUTIONS

RIGHTS OF THE GOVERNMENT

The invention described herein may be manufactured, used, and licensed by or for the U.S. Government for government purposes without the payment to us of any royalty thereon.

BACKGROUND OF THE INVENTION

1. Field of the invention

This invention relates to a method and apparatus for determining aerosol size distributions, and in particular a method and apparatus for determining aerosol size distributions using laser beams.

2. Description of the Prior Art

Various devices have been disclosed in the prior art to determine aerosol size distributions. Often these devices employ Rayleigh-scattering techniques in which a collimated laser beam or a focused tungsten source projects light through aerosol particles. Thereafter the light is scattered by the particles and is collected by a mirror or lens and then relayed to a photocathode of a photo-multiplier. The photo-multiplier current pluses are then amplified, shaped, counted, and histogrammed by appropriate electronic circuitry. The number of counts registered per second then indicates the particle concentration, and the histogram provides a size-frequency distrbution for the detected particles (see U.S. Pat. No 4,071,298 to Falconer). There has previously been developed a method and means for measuring the total particle volume or mass by use of a monochromatic laser light beam directed through a collection of particles and then through a spacial filter which serves to establish a third power relationship between the defracted light flux from each particle transmitted by the spacial filter and the radius of the particle (see U.S. patent application Ser. No. 403,288, now U.S. Pat. No. 3,873,206, filed Oct. 3, 1973 by Wilcock).

Other prior art devices have utilized computation of distribution data by the use of digital computers in systems which laboriously examine individual particles from the collection to be analyzed and use counting procedures to obtain statistics on the aggregate collection.

Yet another metheod and apparatus for particulate monitoring, as disclosed is U.S. Pat. No. 4,015,135 to Tipton, involves illuminating a sample of a suspension having a predetermined known volume containing a particle population sufficiently small to permit substantially simultaneous back-scattered radiation measurement thereof for a given particle classification determination with a monochromatic light source, directing the essentially back-scattered radiation detector along a line substantially coincident with the optical axis of the detector such that the detector transduces the back-scattered radiation from individual particles in the sample into electrical pulse signals, and determining particle size, number and distribution as a function of signal pulse height.

Examples of other relevant particulate and aerosol size distribution monitoring devices can be found in U.S. Pat. No. 4,052,600 to Wertheimer; U.S. Pat. No. 4,037,965 to Weiss; U.S. Pat. No. 4,017,186 to Shofner et al.; U.S. Pat. No. 3,835,315 to Gravitt; U.S. Pat. No. 3,820,897 to Roess; U.S. Pat. No. 3,788,742 to Garbury; U.S. Pat. No. 3,700,333 to Charlson et al.; U.S. Pat. No. 3,646,352 to Bol et al.; and U.S. Pat. No. 3,556,659 to Hawes.

A review, however, of the prior art methods and apparata discussed above reveals that these devices are generally more concerned with particulate rather than aerosol distribution analysis, and often employ highly complex computational techniques requiring sophistacted software and hardware to process the large volumes of data thereby obtained. Even then, however, the final determination of particulate size is often derived from statistical probabilities, based on various assumptions, which can lead to unreliable results.

SUMMARY OF THE INVENTION

Accordingly, one object of this invention is to provide a novel method and apparatus for determining aerosol size distribution using laser beams, which produces improved reliability and accuracy in determining aerosol size distributions.

Another object of this invention is to provide a novel method and apparatus for determining aerosol size distributions, which minimizes the hardware and software requirement for producing the aerosol size distribution.

These and other objectives are achieved according to the invention by directing an amplitude modulated laser beam through the aerosol distribution such that particularly sized aerosol droplets within the electric field of the laser beam cross-sectional area are resonantly elongated in the direction of the electric field. The resonating aerosol droplets of a particular size then mechanically oscillate when the modulation frequency of the laser beam matches the mechanical resonant frequency of the droplet, according to Lord Rayleigh's equation. A second laser beam is then directed against the mechanically oscillating aerosol droplets, and scattered thereby, and monitored. The intensity of the monitored scattered radiation is, however, modulated at the oscillation frequency of the mechanically oscillating droplets, since the resonant elongations produce cyclical changes in the reflective surface area of each resonated drop. Thus, for a given aerosol size distribution the intensity of the scattered sampling laser beam modulated by the mechanical droplet oscillations, is indicative of the relative number of aerosol droplets having a size corresponding to the respective mechanical oscillation. By scanning the modulation frequency of the AM laser beam, and thereby sequentially mechanically resonating appropriately sized droplets corresponding to each particular scanned modulation frequency, a sampling profile can be monitored and the overall aerosol size distribution thereby obtained.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

FIGS. *2a* and *2b* are illustrations of mechanically oscillating aerosol droplets in an aerosol region.

DETAILED DESCRIPTION OF THE PREFERRED EMBODIMENTS

Figure 1:
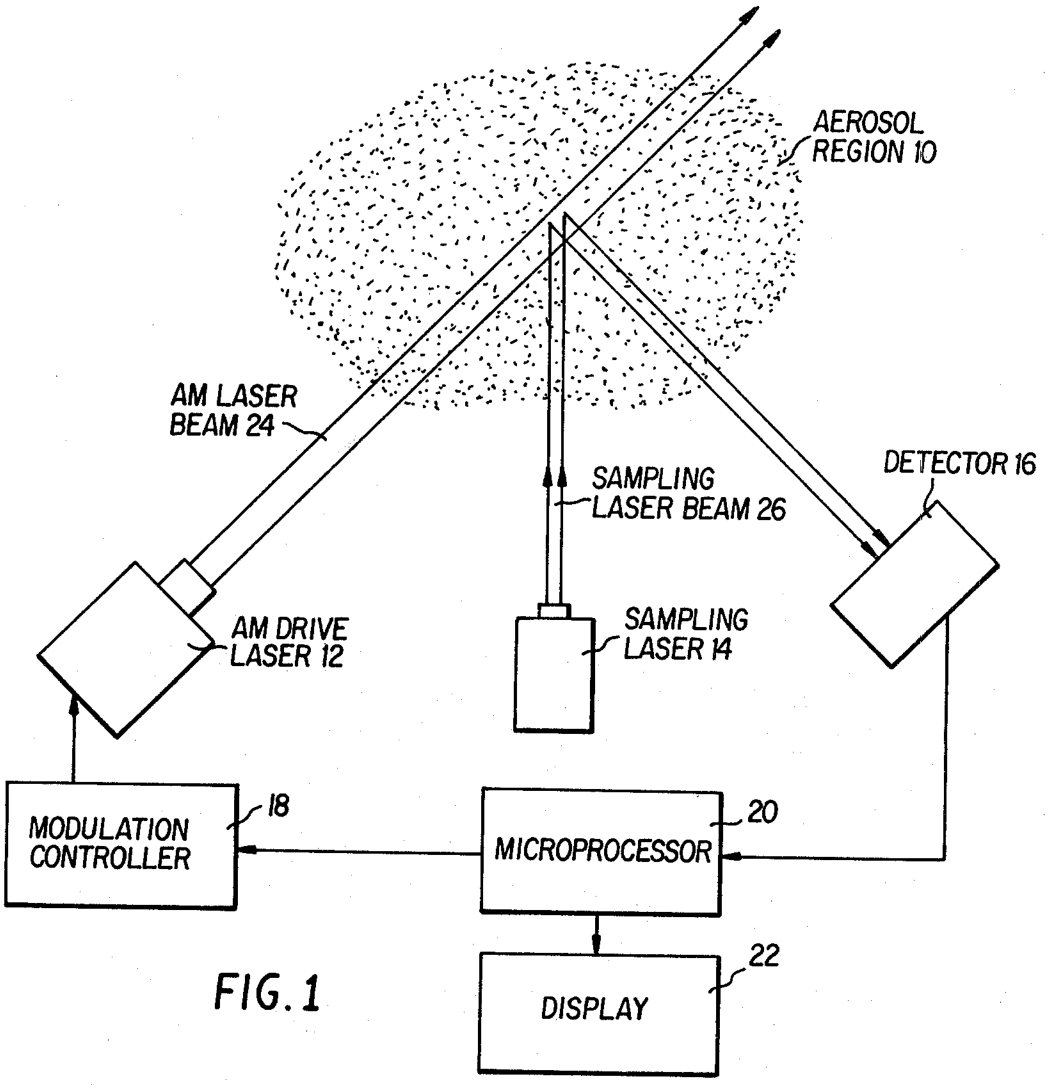
FIG. 1 is a schematic block diagram of the apparatus of the invention.
Figures 2A, 2B:
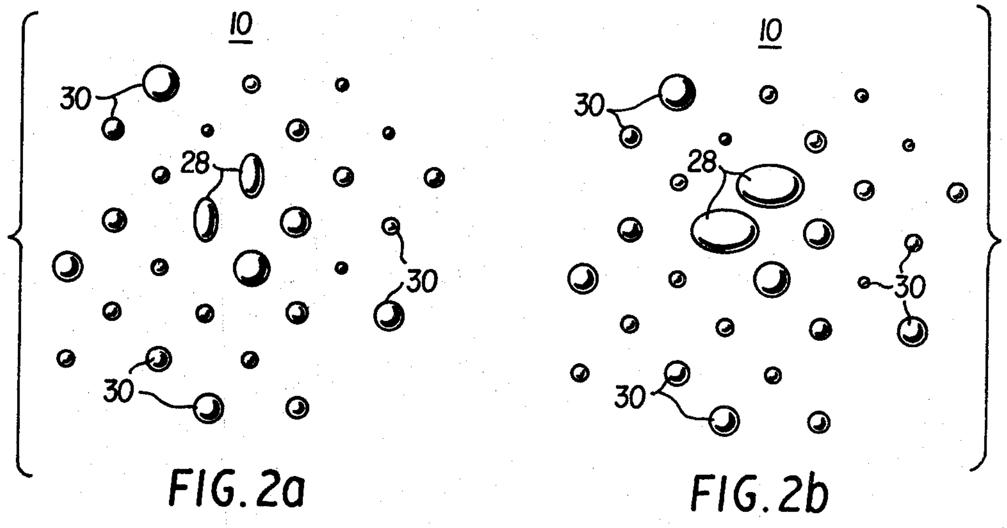

Referring now to the drawings, and more particularly to FIG. 1, the apparatus of the invention for determining the aerosol size distribution of an aerosol region, generally designated as 10, is seen to include an amplitude modulated high power laser 12, a sampling laser 14, a scatter beam detector 16, a modulation controller 18, microprocessor 20, and a display 22. The modulation controller 18 under the control of the microprocessor 20 determines the frequency of the amplitude modulation of the laser 12, such that the modulation frequency of the laser beam 24 produced by the laser 12 is selectively variable over a predetermined frequency range, as determined by the microprocessor 20.

The high power laser 12 generates a high power laser beam 24 which is pointed in the direction of the distribution and directed through the aerosol region 10. The sampling laser 14 is similarly directed such that the output beam 26 thereof intercepts the aerosol region 10 within the beamwidth of the modulated beam 24 of the laser 12. Thus, the laser beam 26 produced by the laser 14 is reflected off aerosol droplets within the beam of the modulation laser 12 towards the beam detector 16. The output of the beam detector 16 is then directed to the microprocessor 20, dedicated to the task of computing the aerosol size distribution based on the intensity of scattered light detected at the detector 16 at the resonant frequency of the aerosol droplet, as determined by the modulating frequency of the amplitude modulated high power laser beam 24.

The present invention is based on the phenomenon that an aerosol droplet placed in an electric field elongates in the direction of the field. The force on an aerosol drop producing the elongation is proportional to the square of the electric field surrounding the drop, since the drop elongates when the field is either "up" or "down". Thus, the force on an aerosol droplet may be defined as, $$F=KE^2 \qquad (1)$$

However, the average force over a period of the laser frequency $T_L$, is given by the following relationship, $$\overline{F(t)} = \frac{1}{T_L}\int_0^{T_L} F(t)dt = K. \qquad (2)$$

If the electric field E of equation 1 is selected as, $$E=E(t)=E_0 \cos\omega t[1+\epsilon_M \cos\omega_M t], \qquad (3)$$

wherein $\epsilon_M$ is the modulation depth and $\omega_M$ is the modulation frequency of an amplitude modulated electric field, E(t), having a carrier frequency ω, the force on an aerosol droplet suspended in the field E (t) depends on the power of the electric field, through the factor $E_0^2$. The time average Poynting vector yields the following relationship, $$E_o = \sqrt{\frac{2Pc}{A}\mu} \qquad (4)$$

where $E_0$ is the electric field, P is the power in watts in the beam of cross sectional area A, $\mu=4\times10^{-7}$ henry/meter, and c is the velocity of light (MKS units). Since in the first equation, K is obtained by minimizing the total mechanical and electrical energy of the system, the force on each aerosol droplet is readily apparent.

If an amplitude modulated laser beam, such as produced by a $CO_2$ laser, is used to generate the electric field given by equation 3 above, and if aerosol drops are immersed in this field, the aerosol drops then resonate when the modulation frequency $\omega_M$ of the electric field E(t) matches the mechanical resonant frequency of the droplet, which was derived by Lord Rayleigh and is defined as follows:

$$\omega_n = \sqrt{\frac{n(n-1)(n+2)\tau}{\rho a^3}} \qquad (5)$$

where n is the resonance mode number, τ is the surface tension, ρ is the density and a is the drop radius. Thus, mechanical resonance of the aerosol droplets at a particular modulation frequency $\omega_M$ is achieved only for those droplets having the requisite radius "a", assuming a dominate oscillation mode (n=2), and a known surface tension τ.

Irradiation by the amplitude modulated beam 24 of laser 12 results in resonant elongation and mechanical oscillation of those aerosol droplets having a size, radius "a", corresponding to the modulation frequency $\omega_M$, which equals $\omega_n$. These oscillating droplets, which generally otherwise have a spheroid shape, then alternately and resonantly elongate and contract between prolate and oblate spheroid states.

FIGS. **2*a* and 2*b* are presented to illustrate the mechanical oscillations of a resonating aerosol droplet 28 between the prolate and oblate spheroid states. Neighboring non-resonant aerosol droplets 30 of different size are seen to be unaffected by the high power amplitude modulated beam 24 of laser 12**.

As a result of the resonance phenomenon, the mechanically oscillating droplets present varying reflective surfaces to the impinging sampling laser beam 26, which results in a varying intensity for a reflected sampling laser beam. Thus, the intensity of the reflected sampling laser beam, is in turn amplitude modulated, with the time varying portion thereof produced by the mechanical oscillations of the resonating droplets.

The intensity of the reflected sample laser beam 26, and more particularly the modulation component thereof, is monitored by the detector 18. Assuming that each resonating aerosol droplet, regardless of size, contributes an identical amounted to the detected modulation component, a quantitative measure of the number of droplets of a particular size is provided at each modulation frequency $\omega_M$. This quantitative measure is produced by the microprocessor 20, as data for each modulation frequency $\omega_M$ is obtained, and a size distribution profile obtained. Additionally, as an added measure of sophistication, the microprocessor 20 can be further programmed to take into consideration the fact that differently sized droplets exhibit reflection surfaces proportional to the square of the radius "a" thereof, resulting in a greater intensity of light reflected from the larger sized droplets. Thus, this factor can easily be compensated for in the data analysis to derive a more accurate aerosol size distribution.

For the purpose of example, only, a $CO_2$ high-power linearly-polarized, amplitude-modulated cw laser can be used for the drive laser 12, while a He-Ne cw laser can be used for the sampling laser 14.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. An apparatus for determining the size distribution of aerosol droplets in an aerosol region, comprising:

drive means for generating an undirectional electric field and directing said field toward said aerosol region such that said field penetrates said aerosol region;

means for amplitude modulating said electric field such that said field is defined by the following relationship, $$E(t)=E_0 \cos\omega t[1+\epsilon_M \cos\omega_M t]$$

1 where $E_0$=peak amplitude $\omega$=carrier frequency $\epsilon_M$=modulation depth $\omega_M$=modulating frequency;

t=time whereby the modulation of said electric field produces resonant elongations and contractions in the form of mechanical oscillations of selectively sized droplets, where the oscillating frequency of said mechanical oscillations is defined by the following relationship, $$\omega_n = \sqrt{\frac{n(n-1)(n+2)\tau}{\rho a^3}} = \omega_M$$

where $\omega_n$=mechanical oscillation frequency n=oscillation mode number $\tau$=droplet surface tension $\rho$=droplet density a=droplet radius;

whereby for a known $\tau$ and $\rho$, and an assumed oscillation mode n, only those droplets having a radius a oscillate at a preselected oscillation frequency $\omega_n$;

sampling means for directing a light beam against the mechanically oscillating aerosol droplets, said sampling means arranged such that said light beam is scattered by said aerosol region with the scattered light beam exhibiting a time varying intensity produced as a result of reflection of said light beam off a time varying droplet reflection surface of each of said oscillating droplets;

detector means in the path of the scattered light beam for measuring the time varying intensity of said scattered light;

data processing means coupled to said amplitude modulating means and said detector means for sequentially selecting the oscillation frequencies $\omega_M$ and for determining an aerosol size distribution based on the intensity of the time varying portion of the scattered light beam at each oscillating frequency $\omega_n$ as measured by said detecting means.

2. An apparatus according to claim 1 wherein said drive means comprises: a $CO_2$ cw-laser.

3. An apparatus according to claim 1 wherein said sampling means comprises:

a He-Ne cw-laser.

4. A method of determining the size distribution of aerosol droplets in an aerosol region, comprising:

generating a unidirectional electric field and directing said field toward said aerosol region such that such field penetrates said aerosol region;

amplitude modulating said electric field such that said field is defined by the following relationships, $$E(t)=E_0 \cos\omega t[1+\epsilon_M \cos\omega_M t]$$

where $E_0$=peak amplitude $\omega$=carier frequency $\epsilon_M$=modulation depth $\omega_M$=modulating frequency t=time whereby the modulation of said electric field produces resonant elongations and contractions in the form of mechanical oscillations of selectively sized droplets, where the oscillating frequency of said mechanical oscillations is defined by the following relationship, $$\omega_n = \sqrt{\frac{n(n-1)(n+2)\tau}{\rho a^3}} = \omega_M$$

where $\omega_n$=mechanical oscillation frequency n=oscillation mode number $\tau$=droplet surface tension $\rho$=droplet density a=droplet radius;

directing a sampling light beam against the mechanically oscillating aerosol droplets such that said light beam is scattered thereby, with the scattered light beam exhibiting a time varying intensity depending on the number of oscillating aerosol droplets;

varying the modulation frequency $\omega_M$ to obtain data indicative of the time varying scattered light intensity of variously sized aerosol droplets with the intensity of the time varying portion of the scattered light beam at each modulation frequency indicative of the number of particularly sized aerosol droplets associated therewith; and, processing said data to obtain an overall size distribution of the droplets in said aerosol region.

* * * * *